United States Patent
Liu et al.

(10) Patent No.: US 8,226,538 B2
(45) Date of Patent: Jul. 24, 2012

(54) BIOMEDICAL USED MULTIPLE-CHANNEL HEMISPHERICAL FOCUSED ULTRASOUND PHASED ARRAY APPARATUS

(75) Inventors: Hao-Li Liu, Tao-Yuan (TW); Jhen-Hao Guo, Tao-Yuan (TW); Heng-Wun Chen, Tao-Yuan (TW)

(73) Assignee: Chang Gung University, Kwei-Shan Tao-Yuan (TW)

( * ) Notice: Subject to any disclaimer, the term of this patent is extended or adjusted under 35 U.S.C. 154(b) by 1260 days.

(21) Appl. No.: 12/000,118

(22) Filed: Dec. 10, 2007

(65) Prior Publication Data

US 2009/0149781 A1 Jun. 11, 2009

(51) Int. Cl.
*A61H 1/00* (2006.01)

(52) U.S. Cl. .............................. 600/2; 600/437; 600/407

(58) Field of Classification Search .................. 600/407, 600/437–461, 300; 601/2; 604/19, 20, 22, 604/606, 601
See application file for complete search history.

(56) References Cited

U.S. PATENT DOCUMENTS

| | | | |
|---|---|---|---|
| 6,561,979 B1 * | 5/2003 | Wood et al. ................... | 600/437 |
| 7,678,048 B1 * | 3/2010 | Urbano et al. ................ | 600/437 |
| 2004/0210135 A1 * | 10/2004 | Hynynen et al. ............. | 600/439 |
| 2008/0294208 A1 * | 11/2008 | Willis et al. .................. | 607/3 |

OTHER PUBLICATIONS

Weng et al., Chen-Yang, "Optimization of Hemispherical Focused Ultrasound Phased Array System for Small-Animal Brain Therapy," Annual Symposium of the Biomedical Engineering, Taipei, Taiwan, Dec. 15, 2006 (5 pp.).

Guo et al., Jhen-Hao, "Microcontroller-Based Control Kernel Design of Multiple-Channel Ultrasound Phased Array Driving System," Annual Symposium of the Biomedical Engineering, Taipei, Taiwan, Dec. 15, 2006 (5 pp.).

Chen et al., Heng-Wun, "A Multiple-Channel Radio-Frequency Driving System Design Based on Programmable Microcontroller Technology," Annual Symposium of the Biomedical Engineering, Taipei, Taiwan, Dec. 15, 2006.

* cited by examiner

*Primary Examiner* — Brian Casler
*Assistant Examiner* — Nasir S Shahrestani
(74) *Attorney, Agent, or Firm* — Bacon & Thomas, PLLC

(57) ABSTRACT

The invention is to a biomedical used multiple-channel hemispherical focused ultrasound phased array apparatus. The invention comprises of a graphic user interface, digital multiple channel phase control kernel, multiple channel driving system, and impedance matching module, power feedback device, as well as the hemispherical low-frequency ultrasound phased array. The invention also serves as a good platform reference to develop a focused ultrasound system in the assisted brain drug delivery application.

2 Claims, 15 Drawing Sheets

BIOMEDICAL USED MULTIPLE-CHANNEL HEMISPHERICAL FOCUSED ULTRASOUND PHASED ARRAY APPARATUS

BACKGROUND OF THE INVENTION

1. Field of the Invention

The invention relates to a biomedical used ultrasound phased array apparatus, particularly to a biomedical used multiple-channel hemispherical focused ultrasound phased array apparatus.

2. Description of the Prior Art

Due to most of human brain surgery is one kind of the invasive-type surgery at present, which accompanies much of therapy risk. Especially most of human brain surgery will destroy the blood-brain barrier, and generates the symptoms such as intracerebral hemorrhage, cerebral vascular accident, infection, destruction of normal nerve fiber and other temporary symptoms, thus the noninvasive therapy is become an important consideration for the medical therapy of human brain. The above-mentioned blood-brain barrier is arranged by the endothelial cell of the brain blood capillary wall mainly, which can transport the material required by the human brain tissue from the blood to the human brain by diffusion, also can protect the human brain at the same time.

The ultrasound therapy is a complete noninvasive-type therapy. Usually the focused ultrasound system is used to focus the energy into the deep part, local part of human body. After the target tissue absorbs the energy focused by the ultrasound, the temperature of local part can raise 30° C. to 55° C. in a short time. The target tissue will be necrosed and coagulated, and the normal front tissue will not be injured. The patients do not need the medical surgery, they can be treated as the clinical case, and the cost of medical therapy can be reduced greatly.

Because of the positioning precision of the focused ultrasound system, its frequency utilization rangy is 0.5 MHz to 3.5 MHz, and its energy focusing point can be controlled in 1 mm to 2 mm. In this range, the frequency can penetrate to certain depth of tissue with very good focusing ability. Thus the cavitation effect caused by the focused ultrasound system can open the blood-brain barrier temporarily. Associating with the guiding and positioning system of the magnetic resonance imaging or the ultrasound imaging etc., the drug can be introduced to brain tissue at local area of human brain precisely, through the temporary opening of blood-brain barrier. Therefore, it is paid attention by the brain surgery, which becomes an important technology for the research of human brain surgery therapy instrument and human brain functionality.

However, due to the focusing ability of low-frequency focused ultrasound system is not reached to the ideal state yet, and the focusing efficiency of single focused ultrasound system is unable to reach to the medical therapy effectively, present ultrasound device is still unable to obtain actual medical efficiency, thus there is a great improvement space.

In the prior art, Taiwan Patent Number 00480335 named as "Method and Device for the Route of Transmission Wave of Focusing Phased Array Used in Spherical Limited Material" is reviewed. This invention relates to a method and device used in the focused ultrasound system, its wave is transmitted from a phased array to a spherical limitation object, so that it can reach to a preset focus at the same time and in the same phase, and detect the crack and structure in object non-destructively. Therefore, said invention does not provide any phase adjustment way, and does not provide the medical use, thus the prior art does not cover the invention.

SUMMARY OF THE INVENTION

The foregoing, as well as additional objects, features and advantages of the invention will be more readily apparent from the following detailed description, which proceeds with reference to the accompanying drawings.

The invention relates to a biomedical used multiple-channel hemispherical focused ultrasound phased array system. The invention comprises of a graphic user interface (GUI), digital multiple channel phase control kernel, multiple channel driving system, phase and wave generator, phase adjustment circuit, power amplifier, impedance matching module, power feedback device, as well as the hemispherical low-frequency ultrasound phased array. It not only can improve the focusing efficiency effectively, but also can disperse the cost of ultrasound phased array, and increase the practicability as well as reduce the manufacturing cost greatly.

The invention also uses the phase adjustment way to make each ultrasound phased array focusing to the same point, in order to improve the drawback that low-frequency ultrasound is not easy to focus naturally.

In the invention, a plurality of 250 KHz flat low-frequency ultrasound phased arrays are arranged as a spherical surface, and the phase of each ultrasound phased array is adjusted to obtain the best focusing efficiency.

The invention uses a phase and wave generator, the main reason is the adjustability of frequency, which is different from the design of high- and low-frequency. It can be operated at higher frequency ultrasound, and can control the output signal more precisely.

The advantages for the ultrasound phased array of the invention are described as follows:

1. The ultrasound phased array is the multiple element cutting, thus each element can control output energy and relative phase difference among elements independently.
2. It can control the location of focusing point precisely, make focus field to conduct electronic scanning, in order to avoid the inconvenience of conventional mechanical driving device and poorer dynamic scanning effect.
3. It can produce more and multiple focusing points for the distribution of ultrasound energy, in order to increase the flexibility of therapy.

In addition, the brain ultrasound therapy of the invention can be used in thermal ablation therapy and drug release, and the application of hemispherical hardware can get more excellent focusing ability.

The invention has a simulation interface to predict the ultrasound field and optimal system disposition, which can simulate various kinds of situation for the manufacturing of medical device in advance, and reduce the development risk in the future.

The invention combines the peripheral interface controller (PIC) and complex programmable logic device (CPLD), which can alter the output frequency arbitrarily, and achieve the phase displacement of multiple channels accurately. The cost of the ultrasound phased array can be reduced through low-cost integrated digital circuit and peripheral interface controller (PIC).

BRIEF DESCRIPTION OF THE DRAWINGS

The foregoing aspects and many of the attendant advantages of this invention will become more readily appreciated as well becomes better understood by reference to the following detailed description, when taken in conjunction with the accompanying drawings, wherein.

DESCRIPTION OF THE PREFERRED EMBODIMENT

The following is a description of the present invention. The invention firstly will be described with reference to one exemplary structure. Some variations will then be described as well as advantages of the present invention. A preferred method of fabrication will then be discussed. An alternate, asymmetric embodiment will then be described along with the variations in the process flow to fabricate this embodiment.

Figure 1:
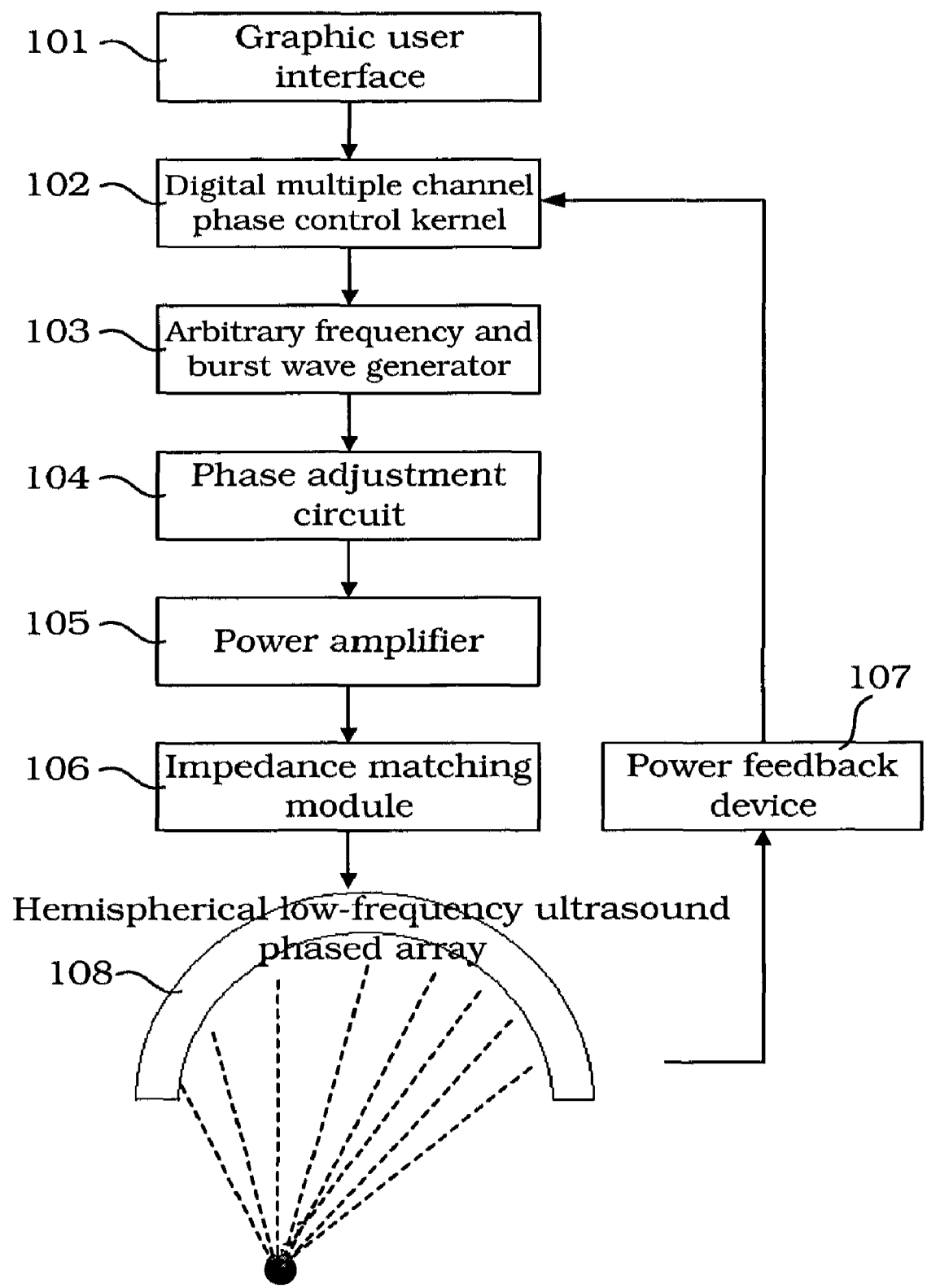
FIG. 1 is the diagram schematically illustrating the embodiment of the invention.

Referring to FIG. 1 for the invention, which is the schematic diagram of the biomedical used multiple-channel hemispherical focused ultrasound phased array system, comprising the following components:

As shown in FIG. 1, the graphic user interface (GUI) 101 is used to emit command and receive signal, thus that the user can understand the predetermined output frequency, wave shape, phase difference of each channel emitted by the computer, observe the power feedback value and adjust the power.

As shown in FIG. 1, the digital multiple channel phase control kernel 102 uses a peripheral interface controller as the control center of whole circuit, to receive various parameters commanded by the computer.

Again, as shown in FIG. 1, the phase and wave generator 103 uses a peripheral interface controller to select and control the generation of clustered wave, and associate with a field-programmable gate array (FPGA) to generate the arbitrary wave.

As shown in FIG. 1, the phase adjustment circuit 104 uses a peripheral interface controller to control and determine the phase difference of each channel, and uses an internal logic phase adjustment circuit of the field-programmable gate array to generate the wave with 8-bit phase resolution. As for the design of phase adjustment circuit of the invention, the square wave should be able to be outputted by the peripheral interface controller, thus the wave is outputted by the coding way. The design principle is to use the input/output port (I/O port) of the peripheral interface controller (PIC) to generate the square wave under continuous change of high voltage level and low voltage level. When the operating speed of oscillator is 32 MHz, the method can generate the 250 KHz square wave with 8-bit phase resolution. The minimum phase difference of each channel is 22.5°. The focus change focus by the 4-bit phase resolution is not precise enough. Thus the phase refining circuit of a D-type flip-flop is introduced to generate the wave with 8-bit phase resolution. The relationship between clock and phase of the D-type flip-flop is shown in Table 1.

TABLE 1

| Phase resolution. | Phase angle | Required clock |
| --- | --- | --- |
| 4 Bit | 22.5° | X |
| 5 Bit | 11.25° | 500 KHz |
| 6 Bit | 5.625° | 1 MHz |
| 7 Bit | 2.8125° | 2 MHz |
| 8 Bit | 1.40625° | 4 MHz |
| 9 Bit | 0.703125° | 8 MHz |

In Table 1, it is found that as long as the speed of D-type flip-flop is quick enough, higher wave phase resolution can be obtained. Even 4 MHz of oscillation frequency is applied, 8-bit phase resolution can be obtained, and the focusing efficiency can be raised greatly.

Again, as shown in FIG. 1, the power amplifier 105 uses full-bridge switching circuit to switch small signal wave into big power wave, in order to drive the hemispherical low-frequency ultrasound phased array.

As shown in FIG. 1, the impedance matching module 106 can use the passive element to carry out the impedance matching precisely, to reduce the reflective power effectively, and lengthen the life of instrument and reduce the failure rate.

As shown in FIG. 1, the power feedback device 107 uses analog/digital transformation element to send the detected power value back to the computer through a peripheral interface controller, so that the user can detect the output power on-time and effectively.

Figure 2A:
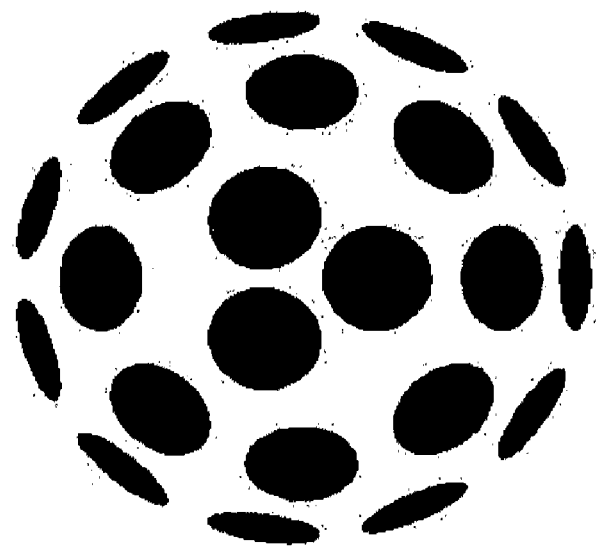
FIG. 2A is the diagram schematically illustrating the first case for the hemispherical cover of the invention.
Figure 2B:
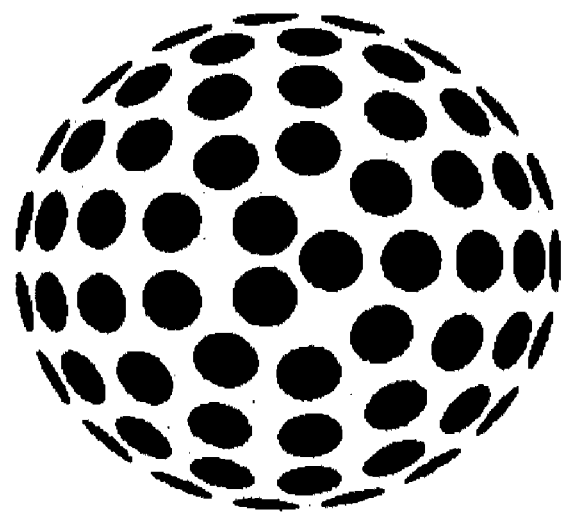
FIG. 2B is the diagram schematically illustrating the second case for the hemispherical cover of the invention.

Finally, as shown in FIG. 1, the hemispherical low-frequency ultrasound phased array 108 is characterized the hemispherical shape with good focusing efficiency. It can disperse the cost of ultrasound phased array effectively, and reduce the manufacturing cost greatly. In the invention, there are two specifications for the hemispherical head cover (used for the installation of phased array). One cover owns 7.5 cm of radius, the other cover has 12.5 cm of radius, 10 and 66 phased arrays are installed, respectively. This is to consider the feasibility of actual hardware and the tolerance of material strength. The first case is shown in FIG. 2A, in which the radius is 7.5 cm with 22 phased arrays. The second case is shown in FIG. 2B, in which the radius is 12 cm with 61 phased arrays.

In FIG. 1, the graphic user interface 101 is connected to the digital multiple channel phase control kernel 102, the phase and wave generator 103, the phase adjustment circuit 104, the power amplifier 105, the impedance matching module 106, the power feedback device 107, and the hemispherical low-frequency ultrasound phased array 108 to form the biomedical used multiple-channel hemispherical focused ultrasound phased array system of the invention.

Figure 3:
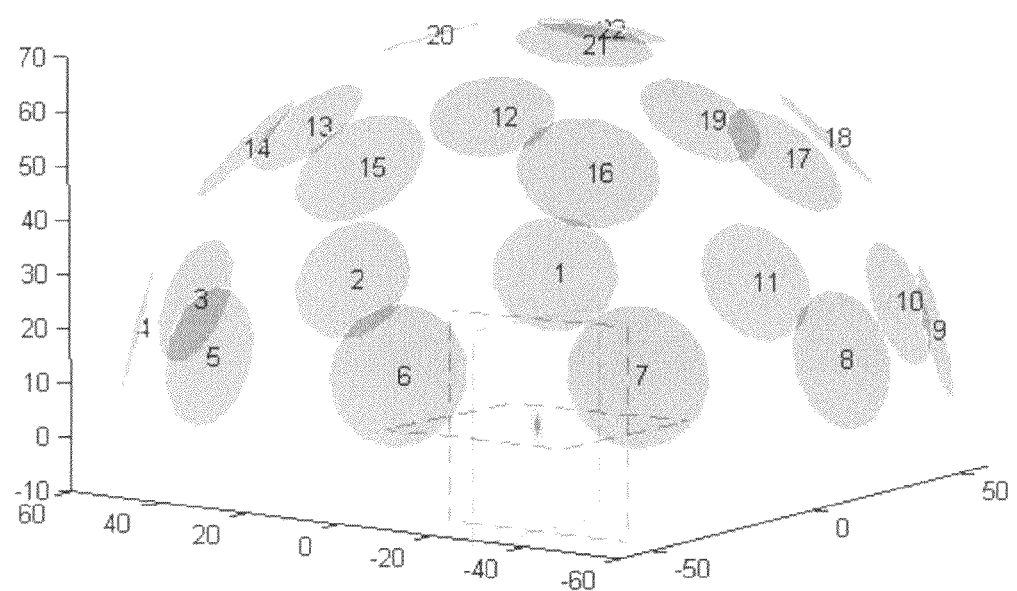
FIG. 3 is the diagram schematically illustrating the three-dimensional result for the experiment of the invention.

Proved by the experiment, the three-dimensional simulation result of the invention is shown in FIG. 3. When the invention is operated actually, the medical device can be used to carry out noninvasive brain surgery of white mouse, and reach the expected goal of the invention.

Figure 4:
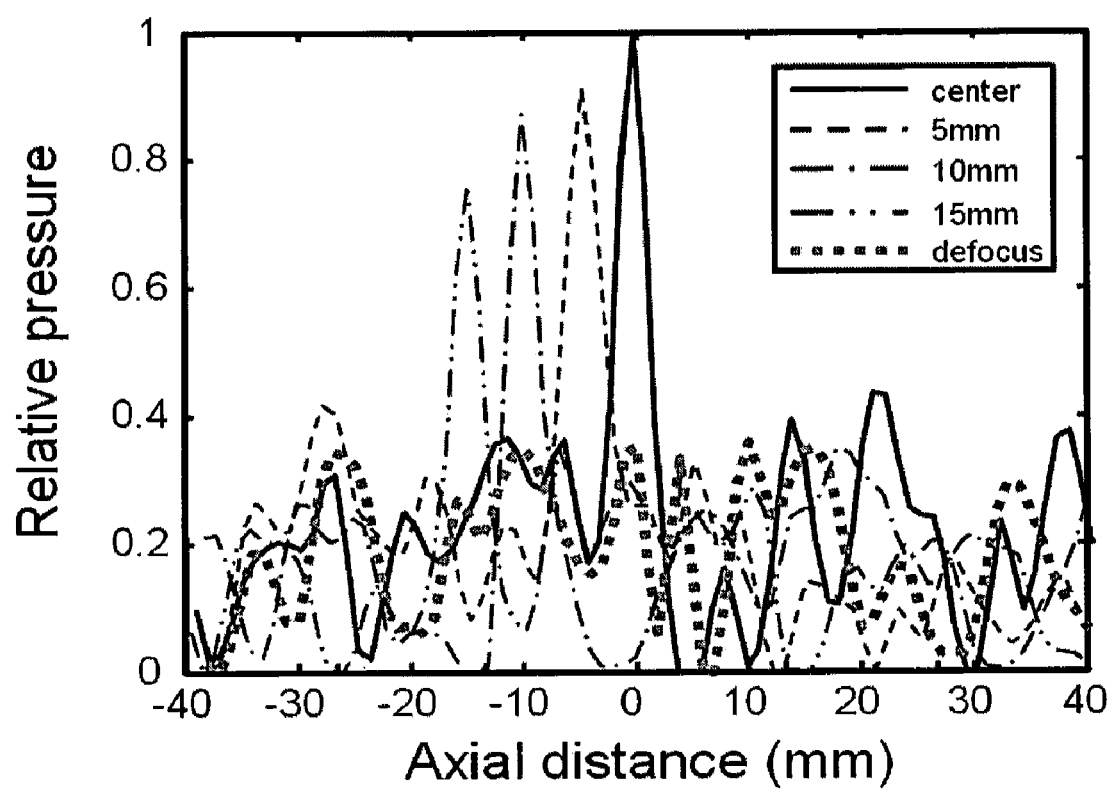
FIG. 4 is the diagram schematically illustrating the experimental result for the dynamic focusing and scanning performance of the phased array of the invention.

As shown in FIG. 4, the experimental result for the dynamic focusing and scanning performance of the phased array of the invention is shown, where the relative pressure is used as y-axis and the axial distance is used as x-axis. From the solid line formed in the diagram, it is found that the invention has better experimental result.

Figure 5A:
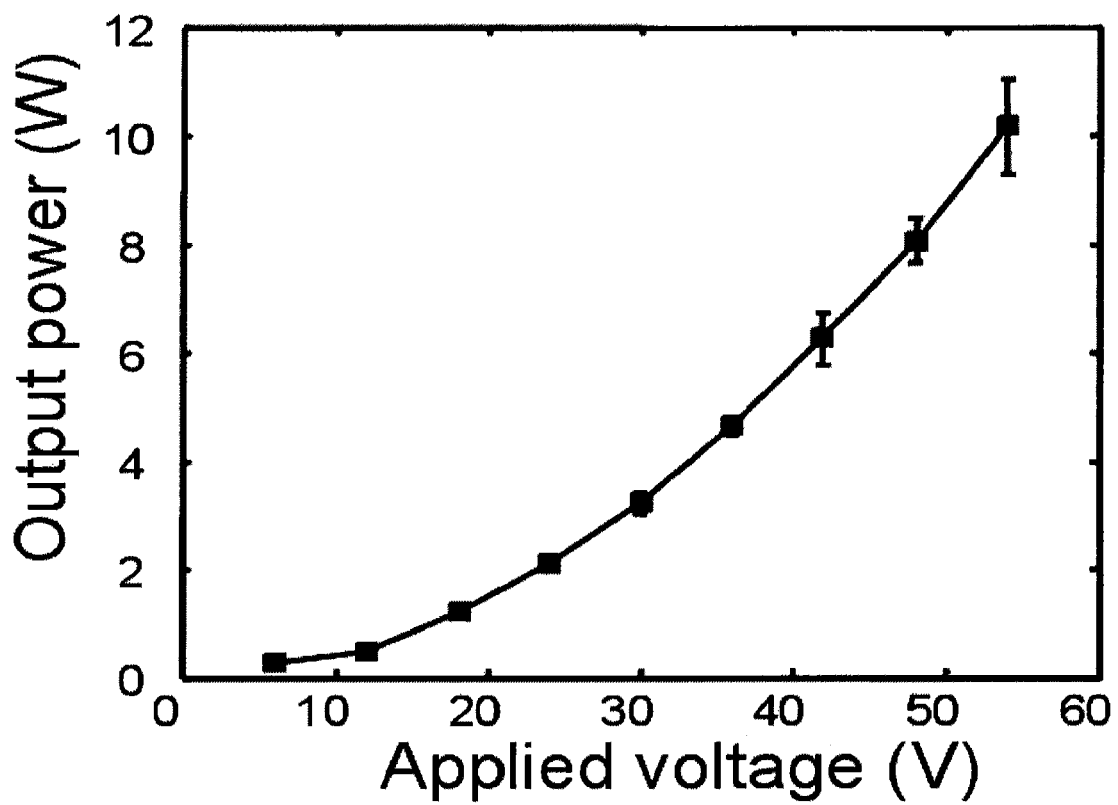
FIG. 5A shows the relationship between the supplied voltage and the net output power.

As shown in FIG. 5A, the relationship between the supplied voltage and the net output power. As the applied voltage increased from 5V to 55 V, the output power increased linearly from 0.3 W to about 10 W, with only small variations among the 31 channels. This indicates that the output power delivered by the system could be monitored simply using a pre-established voltage-to-power lookup table.

Figure 5B:
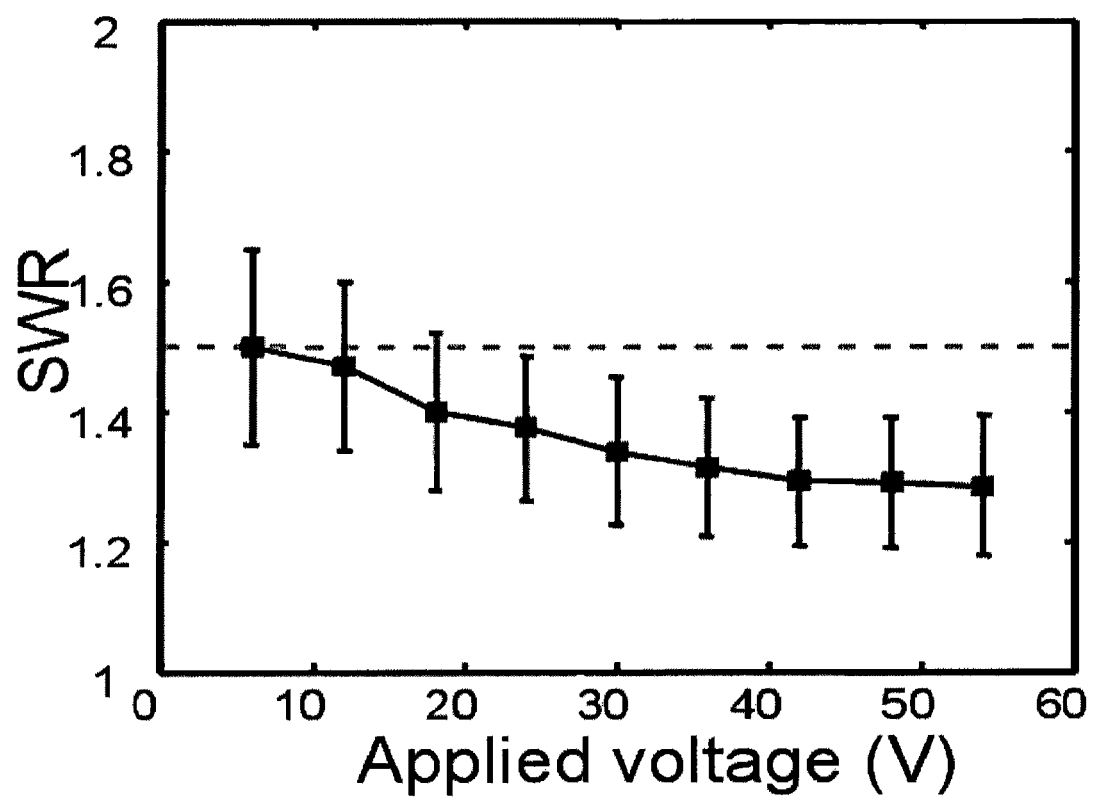
FIG. 5B shows that the SWR can be monitored using the directional coupler.

FIG. 5B further shows that the SWR can be monitored using the directional coupler. The measured SWR is less than 1.5 in most cases, which indicates an electric-to-acoustic efficiency of >95%. The efficiency is lower at small power outputs.

Figure 5C:
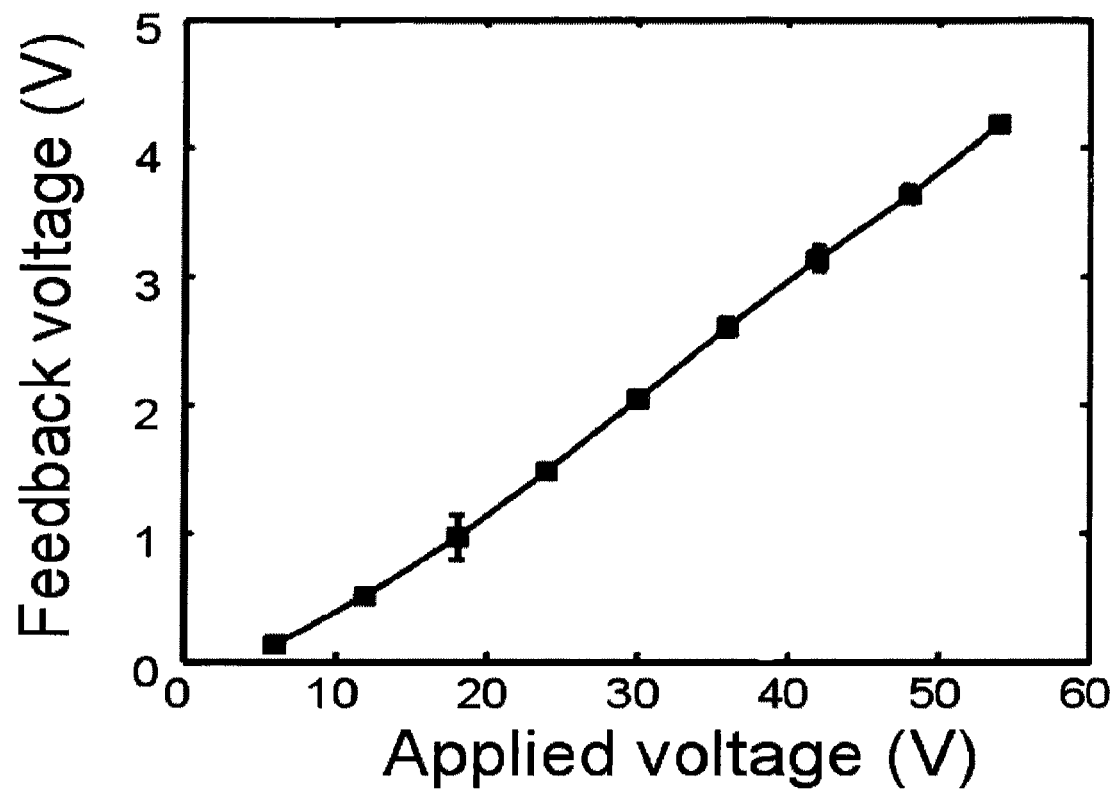
FIG. 5C shows the feedback voltage closely follows the supply voltage.

FIG. 5C shows the feedback voltage closely follows the supply voltage.

Figure 6A:
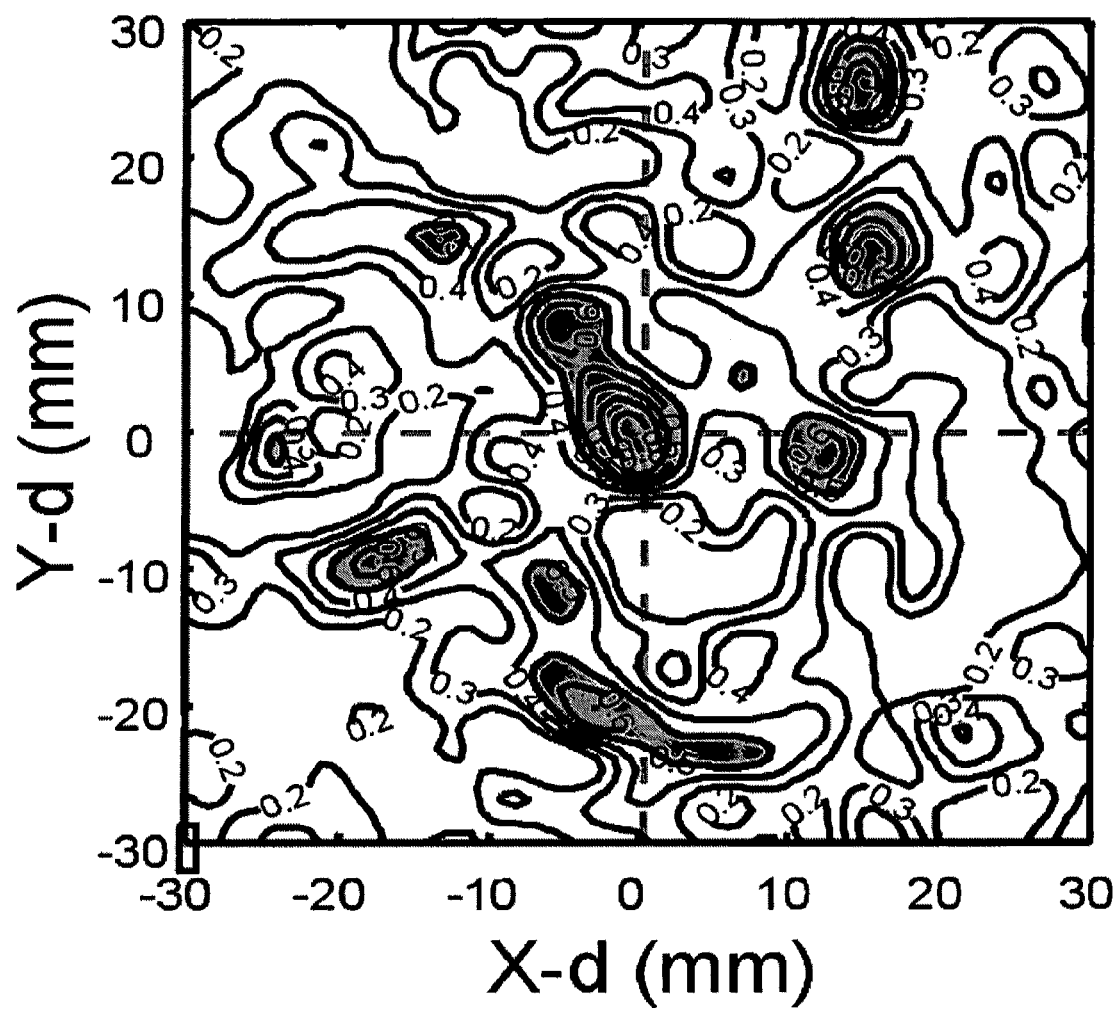
FIG. 6A, FIG. 6B and FIG. 6C illustrate the measured pressure distributions for the 20-, 31-, and 80-element hemispherical arrays along the X-Y plane.
Figure 6B:
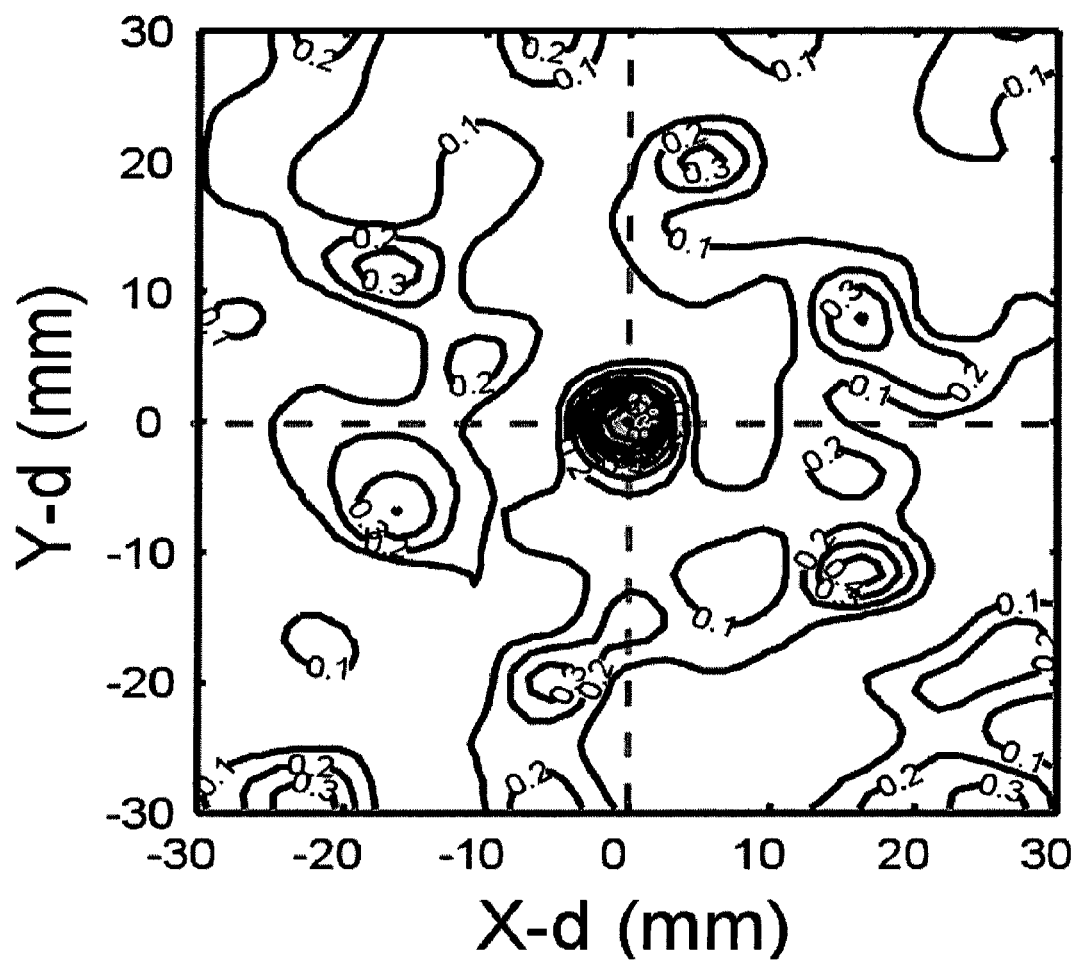
Figure 6C:
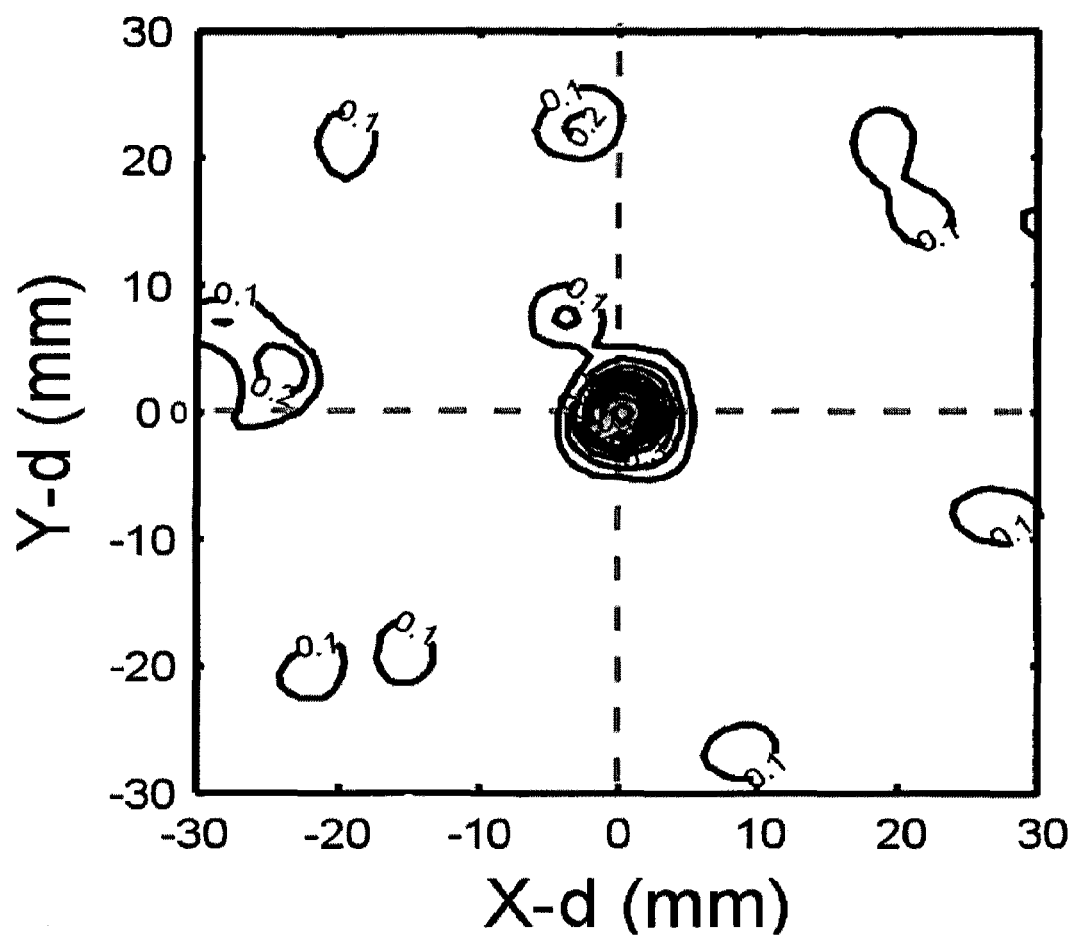

FIG. 6A, FIG. 6B and FIG. 6C illustrate the measured pressure distributions for the 20-, 31-, and 80-element hemispherical arrays along the X-Y plane. It can be seen that a natural focus can be generated without any phase differences.

Figure 7A:
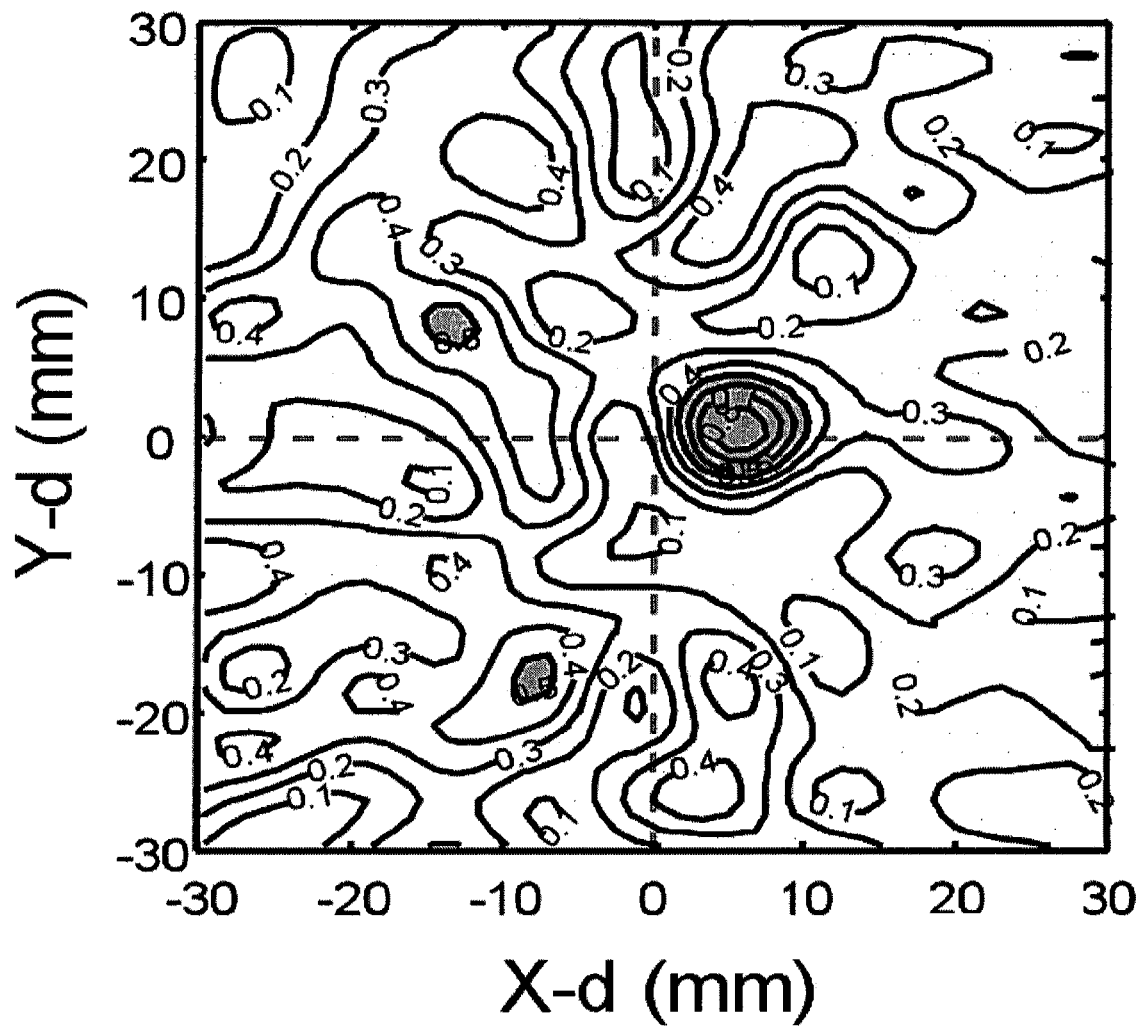
FIG. 7A and FIG. 7B show the two-dimensional (x-y plane) pressure distribution with the steering set to 5 mm and 15 mm off-center.
Figure 7B:
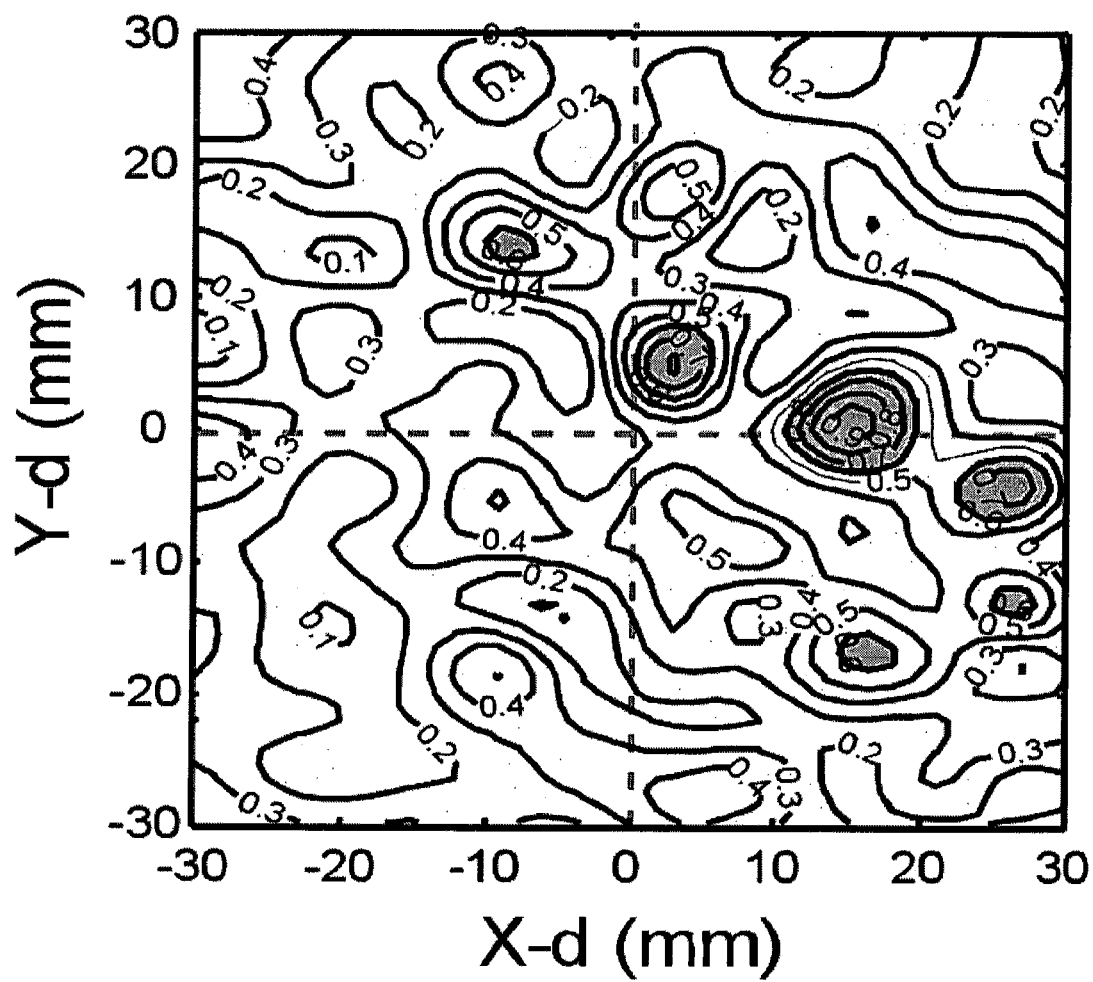

FIG. 7A and FIG. 7B show the two-dimensional (x-y plane) pressure distribution with the steering set to 5 mm and 15 mm off-center.

Figure 8A:
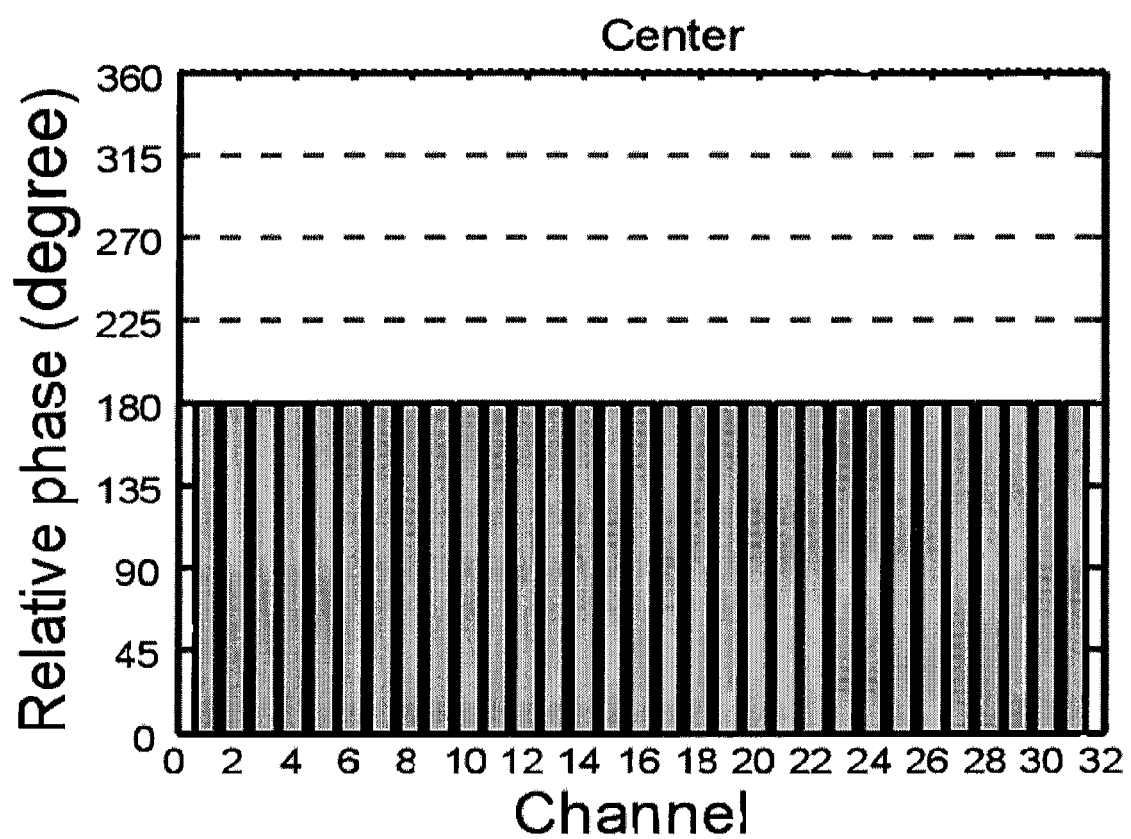
FIG. 8A, FIG. 8B and FIG. 8C show the anesthetized animal in the acrylic holder with the hydrophone attached; and Table 1 shows the relationship between clock frequency and phase of the phase adjustment circuit.
Figure 8B:
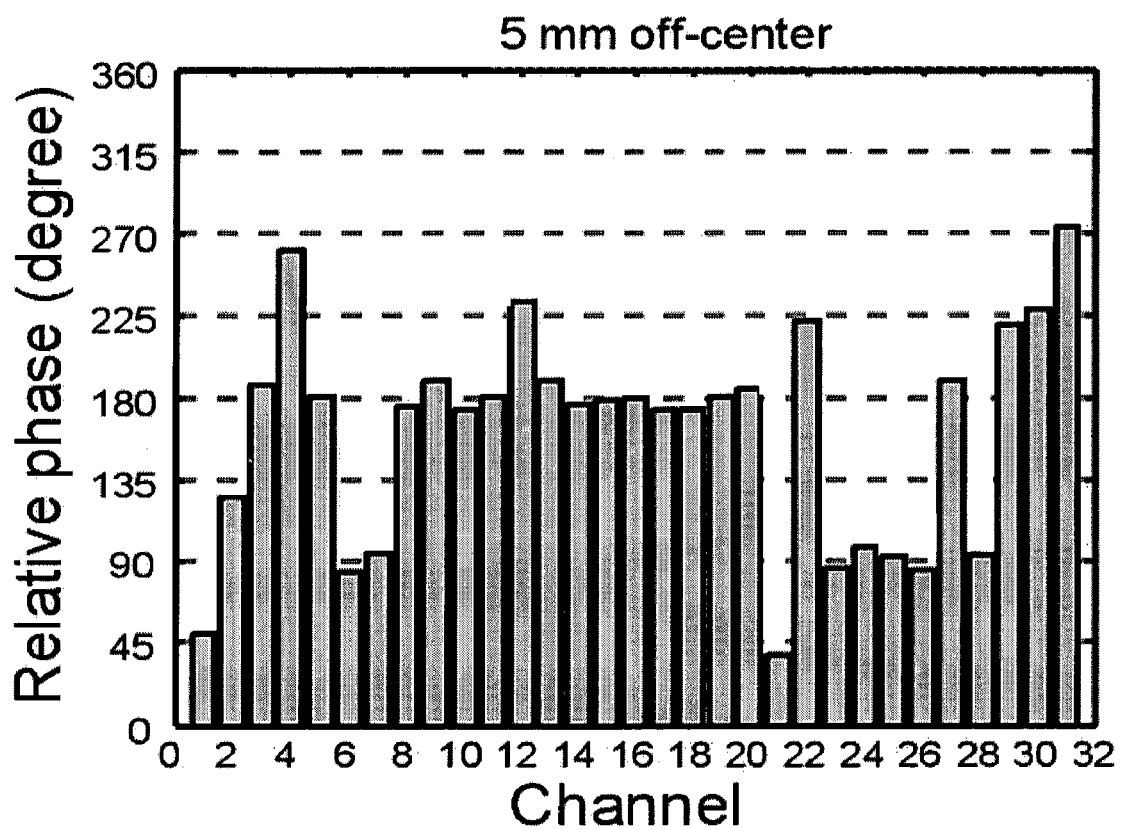
Figure 8C:
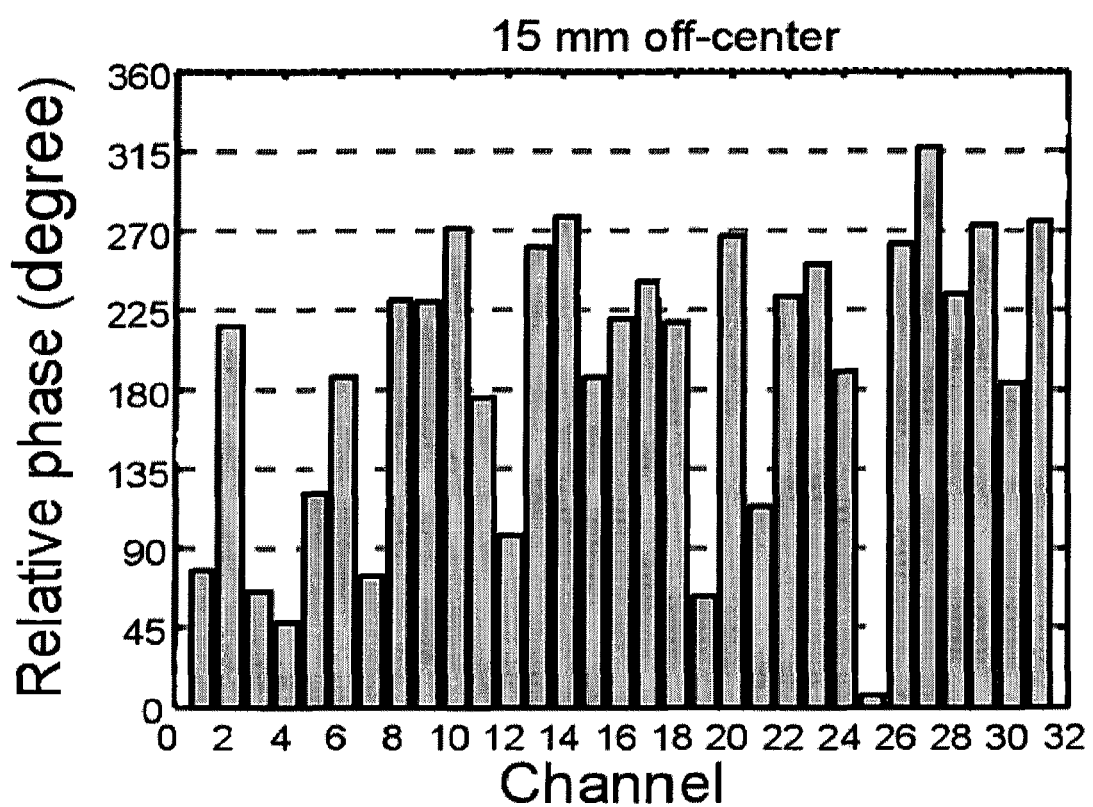

FIG. 8A, FIG. 8B and FIG. 8C show the anesthetized animal in the acrylic holder with the hydrophone attached (10 mm off-center of the holder).

The invention uses the phase adjustment way to make every phased array focusing on the same point, in order to improve the drawback that low-frequency ultrasound is not easy to focus. The low-frequency ultrasound phased array of the invention is the spherical arrangement, and can adjust the phase of each phased array to obtain the best focusing effect. Thus, there are the unique characteristics on the design of phased array system.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A biomedical used multiple-channel hemispherical focused ultrasound phased array apparatus, comprising:

a graphic user interface apparatus means for sending a command and observing a power feedback value and adjusting a power and receiving a signal including a predetermined output frequency, a wave shape, a phase difference of each channel emitted by a computer;

a digital multiple channel phase control kernel means for using a peripheral interface controller as a control center of whole circuits to receive various parameters commanded by the computer;

a phase and wave generator means for using a peripheral interface controller to select and control a generation of clustered wave and associating with a field-programmable gate array to generate a arbitrary wave;

a phase adjustment circuit means for generating a wave with 8-bit phase resolution and a minimum phase difference of each channel being 22.5° wherein using a peripheral interface controller to control a phase difference of a plurality of channels;

a power amplifier means for driving a hemispherical low-frequency ultrasound phased array by using a full-bridge switching circuit to switch a signal wave into a power wave;

an impedance matching module means for using the passive element to carry out an impedance matching to reduce a reflective power and lengthen a life of instrument and reduce a failure rate;

a power feedback device means for detecting the power value and using an analog/digital transformation element to send a detected power value back to the computer through the peripheral interface controller; and a hemispherical low-frequency ultrasound phased array means for characterizing the hemispherical shape and good focusing efficiency, wherein the hemispherical low-frequency ultrasound phased array having 22 phased arrays;

wherein the graphic user interface is connected to the digital multiple channel phase control kernel, the phase and wave generator, the phase adjustment circuit, the power amplifier, the impedance matching module, the power feedback device, and the hemispherical low-frequency ultrasound phased array to form the biomedical used multiple-channel hemispherical focused ultrasound phased array system.

2. The method according to claim 1, wherein the hemispherical low-frequency ultrasound phased array further comprises 61 phased arrays.

* * * * *

UNITED STATES PATENT AND TRADEMARK OFFICE
CERTIFICATE OF CORRECTION

PATENT NO. : 8,226,538 B2
APPLICATION NO. : 12/000118
DATED : July 24, 2012
INVENTOR(S) : Hao-Li Liu et al.

Page 1 of 1

It is certified that error appears in the above-identified patent and that said Letters Patent is hereby corrected as shown below:

Column 6, line 44, please amend claim 2 as follows:

--The ~~method~~ apparatus according to claim 1, wherein the hemispherical low-frequency ultrasound phased array further comprises 61 phased arrays.--

Signed and Sealed this
Nineteenth Day of February, 2013

Teresa Stanek Rea
*Acting Director of the United States Patent and Trademark Office*